(12) United States Patent
Chyba et al.

(10) Patent No.: US 7,125,997 B2
(45) Date of Patent: Oct. 24, 2006

(54) DIFFERENTIAL TUMOR CYTOTOXICITY COMPOUNDS AND COMPOSITIONS

(75) Inventors: Jason Chyba, San Diego, CA (US); Quinn Devereax, San Diego, CA (US); Garret Hampton, San Diego, CA (US); Fred King, Encinitas, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 10/739,667

(22) Filed: Dec. 18, 2003

(65) Prior Publication Data

US 2004/0132786 A1    Jul. 8, 2004

Related U.S. Application Data

(60) Provisional application No. 60/491,132, filed on Jul. 29, 2003, provisional application No. 60/435,853, filed on Dec. 20, 2002.

(51) Int. Cl.
*C07D 241/04* (2006.01)
*C07D 239/24* (2006.01)
*C07D 265/30* (2006.01)
*A61K 31/495* (2006.01)

(52) U.S. Cl. .................. 544/393; 544/166; 544/329
(58) Field of Classification Search ................ 544/393, 544/166, 329; 514/252.12
See application file for complete search history.

(56) References Cited

U.S. PATENT DOCUMENTS 2,766,233 A * 10/1956 Kartinos et al. ......... 548/365.1
3,029,241 A * 4/1962 Otis et al. .................. 544/393
4,336,382 A * 6/1982 Fahrenholtz et al. ........ 544/374
4,931,444 A * 6/1990 Van Wauwe et al. ... 514/254.05
5,728,835 A    3/1998 Aoki et al.
6,013,659 A * 1/2000 Goldfarb et al. ............ 514/367
6,331,555 B1   12/2001 Hirth et al.
6,770,667 B1 * 8/2004 Ito et al. ..................... 514/397
7,001,905 B1 * 2/2006 Biwersi et al. .......... 514/237.5

FOREIGN PATENT DOCUMENTS

CH    0 662 351    * 9/1987
DE    3408127      * 9/1984

OTHER PUBLICATIONS

Valgeirsson et al. 2-Arylureidobenzoic Acids: Selective Non-competitive Antagonists for the Homomeric Kainate Receptor Subtype GluR5. J. Med. Chem. 2003, vol. 46, No. 26, pp. 5834-5843.

* cited by examiner

*Primary Examiner*—Shailendra Kumar
(74) *Attorney, Agent, or Firm*—Genomics Institute of the Novartis Research Foundation; Scott W. Reid

(57) ABSTRACT

The invention is directed to novel biaryl derivatives, to the uses of these compounds in various medicinal applications, including the treatment, prevention and control of proliferative diseases such as tumors, and to pharmaceutical compositions comprising these compounds. Compounds of the invention can be used to treat or prevent diseases or disorders that involve the activity of MIF-1 and/or adenosine kinase.

1 Claim, No Drawings

DIFFERENTIAL TUMOR CYTOTOXICITY COMPOUNDS AND COMPOSITIONS

CROSS-REFERENCE TO RELATED APPLICATIONS

This application claims the benefit of priority to U.S. Provisional Patent Application No. 60/435,853 (filed 20 Dec. 2002) and U.S. Provisional Patent Application No. 60/491,132 (filed 29 Jul. 2003). The full disclosures of these applications are incorporated herein by reference in their entirety and for all purposes.

BACKGROUND OF THE INVENTION

1. Field of the Invention

The invention is directed to novel biaryl derivatives, to the uses of these compounds in various medicinal applications, including the treatment, prevention and control of inflammation and proliferative diseases such as tumors, and to pharmaceutical compositions comprising these compounds. Compounds of the invention can be used to treat or prevent diseases or disorders that involve the activity of MIF-1 and/or adenosine kinase.

2. Background

Cells derived from distinct tumors display common phenomena—a resistance to cell death. This, in part, stems from the fact that tumors can survive an inherent and immunological stimulus to die. Moreover, cells that demonstrate a resistance to chemotherapeutic regimes have often evolved unique solutions for survival; often targeting key regulatory steps in apoptotic programs. Thus, molecules that either exhibit differential cytotoxicity to either tumor cells compared with normal cells or between tumor cells of diverse origin are useful as therapeutic agents in the treatment of proliferative diseases.

SUMMARY OF THE INVENTION

This application relates to differential tumor cytotoxicity compounds of Formula I:

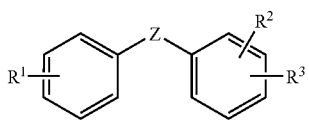

in which:

$R^1$ is selected from the group chosen from hydroxy, $C_{1-6}$alkoxy, halo-substituted-$C_{1-6}$alkoxy and halo-substituted $C_{1-6}$alkyl;

$R^2$ is selected from the group chosen from hydrogen, halo, $C_{1-6}$alkoxy, halo-substituted $C_{1-6}$alkoxy, $C_{1-6}$alkyl and halo-substituted $C_{1-6}$alkyl;

$R^3$ is selected from the group chosen from halo, $C_{1-6}$alkoxy, halo-substituted $C_{1-6}$alkoxy, $C_{1-6}$alkyl, halo-substituted $C_{1-6}$alkyl and —$YNR^4R^5$; wherein Y is a bond or $C_{5-6}$heteroarylene; $R^4$ is selected from the group chosen from hydrogen and $C_{1-6}$alkyl; $R^5$ is $C_{6-10}$aryl substituted with one to three radicals selected from the group chosen from halo, $C_{1-6}$alkyl, $C_{1-6}$alkoxy, halo-substituted $C_{1-6}$alkyl, halo-substituted $C_{1-6}$alkoxy and phenoxy; or $R^4$ and $R^5$ together with the nitrogen to which $R^4$ and $R^5$ are attached form $C_{3-8}$heterocycloalkyl substituted with phenyl optionally substituted with one to three radicals selected from the group chosen from halo, $C_{1-6}$alkoxy, halo-substituted $C_{1-6}$alkoxy, $C_{1-6}$alkyl and halo-substituted $C_{1-6}$alkyl; and Z is —$XNR^6C(O)$—, —$XNR^6C(O)NR^7$— or —$XS(O)_2NR^7$—, wherein X is a bond or $C_{1-6}$alkylene; $R^6$ and $R^7$, independently, is selected from the group chosen from hydrogen and $C_{1-6}$alkyl; and the N-oxide derivatives, pro-drug derivatives, individual isomers and mixture of isomers thereof; and the pharmaceutically acceptable salts and solvates (e.g., hydrates) of such compounds.

A second aspect of the invention is a pharmaceutical composition which contains a compound of Formula I or an N-oxide derivative, individual isomer or mixture of isomers thereof, or a pharmaceutically acceptable salt thereof, in admixture with one or more suitable excipients.

A third aspect of the invention is a method for inhibiting the proliferation of a cancerous cell with compounds of the invention to prevent, inhibit or ameliorate the pathology and/or symptomology of the cancer, which method comprises administering to the animal a therapeutically effective amount of a compound of Formula I and/or a compound of Formula II:

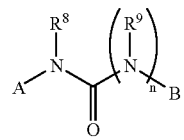

in which:

n is 0 or 1;

A and B, independently is selected from the group chosen from $C_{6-10}$aryl and $C_{5-6}$heteraryl, with the proviso that at least one of A or B is heteroaryl; A and B are optionally substituted with one to three radicals selected from the group chosen from amino, halo, $C_{1-6}$alkoxy, halo-substituted $C_{1-6}$alkoxy, $C_{1-6}$alkyl, halo-substituted $C_{1-6}$alkyl, —$NR^{10}R^{11}$ and —$C(O)OR^{10}$; wherein $R^{10}$ is hydrogen or $C_{1-6}$alkyl; and $R^{11}$ is phenyl optionally substituted with one to three radicals independently selected from the group chosen from halo, $C_{1-6}$alkoxy, halo-substituted $C_{1-6}$alkoxy, $C_{1-6}$alkyl and halo-substituted $C_{1-6}$alkyl; and $R^8$ and $R^9$, independently, is selected from the group chosen from hydrogen and $C_{1-6}$alkyl; or a N-oxide derivative, individual isomer or mixture of isomers thereof; or a pharmaceutically acceptable salt thereof.

A fourth aspect of the invention is the use of a compound of Formula I and/or Formula II in the manufacture of a medicament for treating diseases caused by proliferation of a cancerous cell in an animal.

A fifth aspect of the invention is the use of a compound of Formula I and/or Formula II in the manufacture of a medicament for treating diseases associated with MIF-1 and/or adenosine kinase.

A sixth aspect of the invention is a process for preparing compounds of Formula I and the N-oxide derivatives, pro-drug derivatives, protected derivatives, individual isomers and mixtures of isomers thereof; and the pharmaceutically acceptable salts thereof.

DETAILED DESCRIPTION OF THE INVENTION

The invention provides compounds that are useful in the treatment and/or prevention of diseases or disorders mediated by the proliferation of cancerous cells. Also provided are methods for treating such diseases or disorders.

Definitions

In this specification, unless otherwise defined:

"Aryl" means a monocyclic or fused bicyclic aromatic ring assembly containing six to ten ring carbon atoms. For example, $C_{6-10}$aryl as used in this application, may be phenyl or naphthyl, preferably phenyl. "Arylene" means a divalent radical derived from an aryl group. For example, arylene as used in this application may be phenylene or naphthylene, preferably phenylene, more preferably 1,4-phenylene.

"Heteroaryl" means aryl, as defined in this application, provided that one or more of the ring carbon atoms indicated are replaced by a hetero atom moiety selected from N, O or S, and each ring, unless otherwise specified, is comprised of 5 to 9 ring atoms. For example, $C_{5-6}$heteroaryl as used in this application, includes thiophenyl, pyridinyl, or pyrimidinyl, preferably thiophenyl or pyrimidinyl. "Heteroarylene" means heteroaryl, as defined in this application, provided that the ring assembly comprises a divalent radical.

"Alkyl" as a group and as a structural element of other groups, for example halo-substituted-alkyl or alkoxy, may be either straight-chained or branched. Any cycloalkyl group, alone or as a structural element of other groups may contain from 3 to 8 carbon atoms, preferably from 3 to 6 carbon atoms. Heterocycloalkyl, means cycloalkyl, as defined in this application, provided that one or more of the ring carbon atoms indicated are replaced by a hetero atom moiety selected from N, O or S, and each ring, unless otherwise specified, is comprised of 5 to 9 ring atoms. For example, $C_{3-8}$heterocycloalkyl as used in this application, includes morpholino, piperidinyl or piperazinyl, preferably morpholino.

"Halo" or "halogen" means F, Cl, Br or I, preferably F or Cl. Halo-substituted alkyl groups and compounds may be partially halogenated or perhalogenated, whereby in the case of multiple halogenation, the halogen substituents may be identical or different. A preferred perhalogenated alkyl group is for example trifluoromethyl.

DESCRIPTION OF THE PREFERRED EMBODIMENTS

The invention provides compounds that are useful in the treatment and/or prevention of diseases or disorders mediated by the proliferation of cancerous cells. In one embodiment, for compounds of Formula I, $R^1$ is selected from the group chosen from hydroxy, morpholino, methoxy and trifluoromethyl. Preferably, $R^2$ is selected from the group chosen from hydrogen, halo, hydroxy, triflouromethoxy and trifluoromethyl.

In another embodiment, $R^3$ is halo, triflouromethoxy, trifluoromethyl or —YNR$^4$R$^5$, preferably —YNR$^4$R$^5$. Y is a bond or pyrimidinylene, preferably 4,6-pyrimidinylene. $R^4$ is preferably hydrogen.

In a further embodiment, $R^5$ is phenyl substituted with one to three groups selected from halo, $C_{1-6}$alkyl, trifluoromethyl, triflouromethoxy and phenoxy, more preferably triflouromethoxy. More preferably, $R^4$ and $R^5$ together with the nitrogen to which they are attached form piperazinyl substituted with phenyl optionally substituted with halo, trifluoromethyl or triflouromethoxy. Preferably, phenyl is optionally meta substituted.

In another embodiment, Z is preferably —XNHC(O)—, —XNHC(O)NH— or —XS(O)$_2$NH—, wherein X is a bond, methylene, ethylene or propylene. More preferably, X is a bond, methylene or ethylene.

The invention further provides a method of inhibiting proliferation of a cancerous cell, the method comprising contacting the cell with a compound of Formula I and/or Formula II. In one embodiment, the cell is in a mammal. In another embodiment, the mammal is a human. In another embodiment a method is provided for treating cancer in a mammal, the method comprising administering to the mammal a therapeutically effective amount of a compound of Formula II.

In another embodiment, for compounds of Formula II:

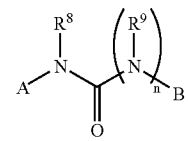

n is 0 or 1; A and B, are independently selected from the group chosen from phenyl, pyridine, thiophene and furan, with the proviso that at least one of A or B is heteroaryl; A and B are optionally substituted with one to three groups selected from the group chosen from amino, halo, methoxy, triflouromethoxy, $C_{1-6}$alkyl, —NR$^{10}$R$^{11}$, —OR$^{11}$ and —C(O)OR$^{10}$; wherein R$^{10}$ is hydrogen, methyl or ethyl; and R$^{11}$ is phenyl optionally substituted with one to three radicals independently selected from the group chosen from halo, $C_{1-6}$alkoxy, halo-substituted $C_{1-6}$alkoxy, $C_{1-6}$alkyl and halo-substituted $C_{1-6}$alkyl; and R$^8$ and R$^9$ are both hydrogen.

More preferred are compounds of formula II selected from the group chosen from 1-(2,6-dimethoxy-pyridin-3-yl)-3-(4-trifluoromethoxy-phenyl)-urea, 5-(3-amino-phenylcarbamoyl)-2-(3-fluoro-benzoylamino)-4-methyl-thiophene-3-carboxylic acid methyl ester and furan-2-carboxylic acid [6-(4-tert-butyl-phenoxy)-pyridin-3-yl]-amide.

A further embodiment of the invention provides for a method of inhibiting proliferation of a cancerous cell, the method comprising contacting the cell with a compound selected from the group chosen from 1-{4-[2-(3-chloro-phenylamino)-pyrimidin-4-yl]-pyridin-2-yl}-1-(3-ureido-propyl)-urea, 2,2-dimethyl-propionic acid 4-[3-(3,4-dimethyl-phenyl)-isoxazol-5-yl]-2H-114-thiazol-2-ylmethyl ester and 2,2-dimethyl-propionic acid 4-[3-(3,4-dimethyl-phenyl)-isoxazol-5-yl]-thiazol-2-ylmethyl ester.

In another embodiment, the cell is in a mammal. In a further embodiment, the mammal is a human. In yet a further embodiment a method is provided for treating cancer in a mammal, the method comprising administering to the mammal a therapeutically effective amount of 1-{4-[2-(3-chloro-phenylamino)-pyrimidin-4-yl]-pyridin-2-yl}-1-(3-ureido-propyl)-urea, 2,2-dimethyl-propionic acid 4-[3-(3,4-dimethyl-phenyl)-isoxazol-5-yl]-2H-114-thiazol-2-ylmethyl ester or 2,2-dimethyl-propionic acid 4-[3-(3,4-dimethyl-phenyl)-isoxazol-5-yl]-thiazol-2-ylmethyl ester.

Compounds of the present invention are often active with free hydroxyl and free amine groups. Forms of the compound that have the hydroxyl or amine group present in a protected form often function as prodrugs. Prodrugs are compounds that are converted into an active drug form after administration, through one or more chemical or biochemical transformations. Forms of the compounds of the present invention that are readily converted into the claimed compound under physiological conditions are prodrugs of the claimed compounds and are within the scope of the present invention. Examples of prodrugs include forms where a hydroxyl group is acylated to form a relatively labile ester such as an acetate ester, and forms where an amine group is acylated with the carboxylate group of glycine or an L-amino acid such as serine, forming an amide bond that is particularly susceptible to hydrolysis by common metabolic enzymes. The present invention also includes both enzymatically phosphorylated or dephosphorylated compounds, optionally in equilibrium.

Compounds of the invention may exist in free form or in salt form, e.g. addition salts with inorganic or organic acids, an ammonium salt or salts with metals such as sodium, potassium, calcium, zinc or magnesium, or a mixture thereof. Compounds of formula I, and their salts in hydrate or solvate form, are also part of the invention.

When the compounds of the invention have asymmetric centers in the molecule, various optical isomers are obtained. The present invention also encompasses enantiomers, racemates, diastereoisomers and mixtures thereof. Moreover, when the compounds of the invention include geometric isomers, the present invention embraces cis-compounds, trans-compounds and mixtures thereof. Similar considerations apply in relation to starting materials exhibiting asymmetric carbon atoms or unsaturated bonds as mentioned above.

The compounds of the invention are useful for treating diseases in which abnormal cellular proliferation contribute to the pathology and/or symptomology of a disease. For example, the compounds of the invention are suitable for the treatment of proliferative diseases, especially tumor diseases, including metastases; for example solid tumors such as lung tumors, breast tumors, colorectal tumors, prostate tumors, melanomas, brain tumors, pancreatic tumors, neck tumors, bladder tumors, neuroblastomas, throat tumors, but also proliferative diseases of blood cells, such as leukemia. The cytotoxic activities of the compounds of the invention can be determined by methods known to those of ordinary skill in the art. Suitable in vitro assays for measuring cellular activity and the cytotoxicity of compounds of the invention are detailed below.

The invention also relates to inhibiting the action of Macrophage Migration Inhibitory Factor (MIF), especially MIF-1. In response to antigenic or mitogenic stimulation, lymphocytes secrete protein mediators called lymphokines that play an important role in immunoregulation, inflammation and effector mechanisms of cellular immunity, (Miyajima, A., et al., FASEB J., 38:2462–2473 (1988)). The first reported lymphokine activity was observed in culture supernatants of antigenically sensitized and activated guinea pig lymphocytes. This activity was named migration inhibitory factor (MIF) for its ability to prevent the migration of guinea pig macrophages out of capillary tubes in vitro, (Bloom, B. R., et al., Science, 153:80–82 (1966)). MIF is produced by activated T cells and is a major secreted protein released by the anterior pituitary cells. The detection of MIF activity is correlated with a variety of inflammatory responses including delayed hypersensitivity and cellular immunity (Rocklin, R. E. et al., New England J. Med., 282:1340–1343 (1970); allograft rejection (Al-Askari, S. et al., Nature, 205:916–917 (1965); and rheumatoid polyarthritic synovialis (Odink et al., Nature, 330:80–82 (1987). MIF-1 has also oxidoreductase (Kleemann, R. et al., J. Mol. Biol., 1998, 280, 85–102), tautomerase enzyme activity (Dios, A., et al., J. Med. Chem., 2002, 45, 2410–2416) and plays an important role in carcinogenesis (Fingerle-Rowson, G. et al., PNAS, Aug. 5, 2003, vol. 100, no. 16, 9354–9359).

Compounds of the invention inhibit MIF function, particularly MIF-1, and are thus suitable for treatment of MIF mediated diseases such as inflammatory disorders (e.g., Sepsis, Rheumatoid arthritis), immune disorders, transplantation rejection and arthritis and cancer.

The invention also relates to inhibiting the action of peroxiredoxins. Peroxiredoxins are involved in many cellular metabolic and signaling processes by controlling the levels of intracellular reactive oxygen species (ROS). ROS are thought to have a role in disease, particularly in carcinogenesis and ageing. MIF-1 has been demonstrated to bind to peroxiredoxin and regulate its activity.

Compounds of the invention indirectly inhibit peroxiredoxins by regulating MIF-1 function. Thus, they are suitable for treatment of diseases mediated by peroxiredoxins such as cancer and ageing.

The invention also relates to inhibiting the action of adenosine kinase. Adenosine kinase is a cytostolic enzyme that catalyzes the phosphorylation of adenosine to AMP. Inhibition of adenosine kinase can potentially reduce the ability of the cell to utilize adenosine, leading to increased adenosine outside of the cell where it is pharmacologically active.

Adenosine plays a major role in a variety of important cellular processes. It is a vasodilator, can inhibit immune function, enhance activation of mast cells (associated with allergic reactions), inhibit neutrophil oxygen free radical production, is antiarrhythmic, and is an inhibitory neurotransmitter. Adenosine is phosphorylated to adenosine monophosphate (AMP) by adenosine kinase. Ultimately, the AMP that is produced via adenosine kinase is converted to adenosine triphosphate (ATP) that is used by all cells to store energy for use in future energy-utilizing metabolic reactions or mechanical work (e.g. muscle contraction). Extracellular adenosine, frequently produced by breakdown of intracellular ATP pools, evokes a variety of pharmacological responses through activation of extracellular adenosine receptors located on the surface of nearly all cells. For example, adenosine produces a variety of cardiovascular related effects including vasodilation, inhibition of platelet aggregation, and negative inotropic, chronotropic and domotropic effects on the heart. Adenosine also has effects within the central nervous system (CNS) including inhibition of neurotransmitter release from presynaptic neurons and inhibition of post-synaptic neuron firing in brain and the spinal cord and at sites of inflammation, such as inhibition of neutrophil adhesion to endothelial cells and inhibition of neutrophil oxygen free-radical production.

The action of compounds of the invention that result in an increase of extracellular adenosine can be beneficial to living organisms, particularly under certain conditions. For example, compounds that increase adenosine levels have been associated with the treatment of ischemic conditions such as stroke, as well as other conditions benefited by enhanced adenosine levels.

Compounds of the invention inhibit Adenosine kinase and are thus suitable for treatment of Adenosine kinase mediated diseases or disorders such as: chronic neurodegenerative diseases, such as Alzheimer's disease, Parkinson's disease, ALS, Huntington's disease, and AIDS dementia; seizure disorders and other neurological disorders such as epilepsy; cardiovascular and cerebrovascular diseases; inflammation; arthritis; acute pain, including but not limited to perioperative, post-surgical, and end-stage cancer pain, pain caused by arthritis, cancer, trigeminal neuralgia, multiple sclerosis, neuropathies such as those arising from diabetes and AIDS and in addition, lower back pain and phantom limb pain; muscle relaxants; inducing sleep and other diseases or disorders which can be regulated by increasing the local concentration of adenosine.

In general, compounds of the invention will be administered in therapeutically effective amounts via any of the usual and acceptable modes known in the art, either singly or in a combination with one or more therapeutic agents. A therapeutically effective amount may vary widely depending on the severity of the disease, the age and relative health of the subject, the potency of the compound used and other factors. For example, therapeutically effective amounts of a compound of the invention may range from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 1 to 50 mg active ingredient.

The compounds of the invention may be administered by any conventional route, in particular enterally, for example, orally, e.g. in the form of tablets or capsules, or parenterally, for example, in the form of injectable solutions or suspensions, topically, e.g. in the form of lotions, gels, ointments or creams, or in a nasal or a suppository form. Pharmaceutical compositions comprising a compound of the invention in free form or in pharmaceutically acceptable salt form in association with at least one pharmaceutical acceptable carrier or diluent may be manufactured in a conventional manner by mixing with a pharmaceutically acceptable carrier or diluent.

The compounds of the invention may be administered in free form or in pharmaceutically acceptable salt form, for example, as indicated above. Such salts may be prepared in a conventional manner and exhibit the same order of activity as the free compounds.

In accordance with the foregoing the present invention further provides:

1. A method for preventing or treating proliferative diseases, e.g. such as tumors, in a subject in need of such treatment, which method comprises administering to said subject an effective amount of a compound of the invention or a pharmaceutically acceptable salt thereof;

2. A method for preventing or treating diseases e.g. as indicated above, in a subject in need of such treatment, which method comprises administering to said subject an effective amount of a compound of the invention or a pharmaceutically acceptable salt thereof;

3. A compound of the invention, in free form or in a pharmaceutically acceptable salt form for use as a pharmaceutical, e.g. in any of the methods as indicated under 1 or 2 above;

4. A pharmaceutical composition, e.g. for use in any of the methods as in 1 or 2 above, comprising a compound of the invention in free form or pharmaceutically acceptable salt form in association with a pharmaceutically acceptable diluent or carrier thereof; and 5. A compound of the invention, or a pharmaceutically acceptable salt thereof, for use in the preparation of a pharmaceutical composition for use in any of the methods as in 1 or 2 above.

The compounds of the invention may be administered as the sole active ingredient or in conjunction with, for example as an adjuvant to, other drugs such as a chemotherapeutic agent, for example a malignant cell anti-proliferative agent. For example, the compounds of the invention may be used in combination with a chemotherapeutic agent, for example paclitaxel, gemcitabine, cisplatinum, doxorubicin or 5-fluorouracil.

Where the compounds of the invention are administered in conjunction with other chemotherapeutic therapy, dosages of the co-administered chemotherapeutic compound will of course vary depending on the type of co-drug employed. In accordance with the foregoing the present invention provides in a yet further aspect:

6. A method as defined above comprising co-administration, for example concomitantly or in sequence, of a therapeutically effective non-toxic amount of a compound of the invention and at least a second drug substance, for example a chemotherapeutic drug, for example as indicated above; and 7. A pharmaceutical combination, for example a kit, comprising a) a first agent which is a compound of the invention as disclosed herein, in free form or in pharmaceutically acceptable salt form, and b) at least one co-agent, for example a chemotherapeutic drug. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, for example a compound of formula I and a co-agent, are both administered to a patient simultaneously in the form of a single entity or dosage. The term "non-fixed combination" means that the active ingredients, for example a compound of the invention and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, for example the administration of 3 or more active ingredients.

Methods for Preparing Compounds of the Invention

The present invention also includes a process for the preparation of a compound of the invention. In the reactions described, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for example, see T. W. Greene and P. G. M. Wuts in "Protective Groups in Organic Chemistry", John Wiley and Sons, 1991.

Compounds of Formula I, wherein Z has a —XNR⁶C(O)— linkage, can be prepared by proceeding as in the following Reaction scheme 1:

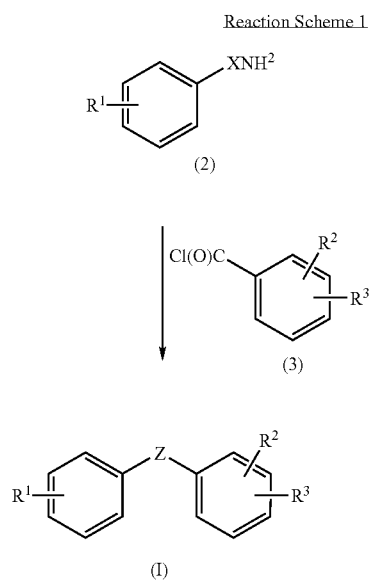

in which R¹, R², R³ and X are as defined for Formula I above.

Compounds of Formula I can be prepared by coupling a compound of Formula 2 with a compound of Formula 3. The coupling reaction can be effected in a suitable base (e.g., triethylamine, diethylpropylethylamine, DMAP, or the like) at ambient temperature and can take 1 to 20 hours to complete.

Compounds of Formula I, wherein Z has a —XNR⁶C(O)— linkage, can be prepared by proceeding as in the following Reaction scheme 2:

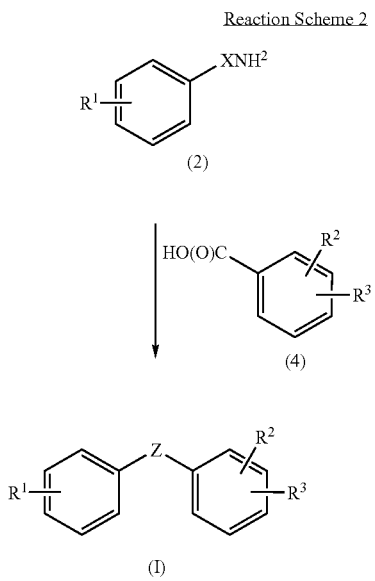

in which R¹, R², R³ and X are as defined for Formula I above.

Compounds of Formula I can be prepared by condensing a compound of Formula 2 with a compound of Formula 4. The reaction can be effected by an appropriate coupling agent (e.g., EDCI, HATU, PyBOP, or the like) and a suitable base (e.g., triethylamine, diethylpropylethylamine, DMAP, or the like) at ambient temperature and can take 5 to 20 hours to complete.

Compounds of Formula I can be prepared by proceeding as in the following Reaction scheme 3:

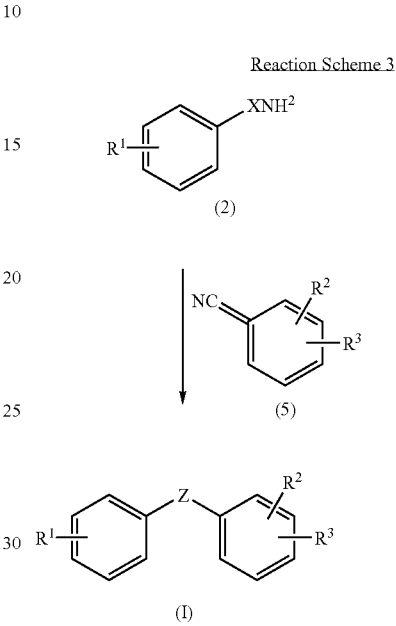

in which R¹, R², R³ and X are as defined for Formula I above.

Compounds of Formula I can be prepared by reacting a compound of Formula 2 with a compound of Formula 5. The reaction can be effected in a suitable base (e.g., triethylamine, diethylpropylethylamine, DMAP, or the like) at ambient temperature and can take 1 to 10 hours to complete.

Detailed descriptions for the synthesis of a compound of Formula I by the processes in reaction schemes 1, 2 and 3 are set forth in the examples, below.

Additional Processes for Preparing Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T W. Greene, "Protecting Groups in Organic Chemistry", 3$^{rd}$ edition, John Wiley and Sons, Inc., 1999.

Compounds of the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferable, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from the their racemic mixture can be found in Jean Jacques, Andre Collet, Samuel H. Wilen, "Enantiomers, Racemates and Resolutions", John Wiley And Sons, Inc., 1981.

In summary, the compounds of Formula I are made by a process which comprises:

(a) reacting, according to reaction schemes 1, 2 or 3 above, a compound of Formula (2):

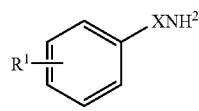

(2)

with a compound of Formula (3), (4) or (5):

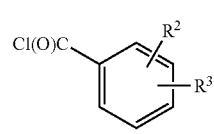

(3)

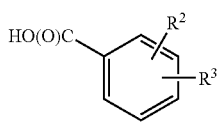

(4)

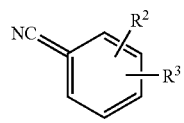

(5)

in which R$^1$, R$^2$, R$^3$ and X are as defined for Formula I above.

(b) optionally converting a compound of the invention into a pharmaceutically acceptable salt; or (c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or may be prepared analogously to methods known in the art or as disclosed in the Examples, below. One of skill in the art will appreciate that the above transformations are only representative of methods for preparation of the compounds of the present invention, and that other well known methods can similarly be used. The following Examples provide detailed descriptions of the preparation of representative compounds of the present invention.

EXAMPLE 1

N-(4-Morpholin-4-yl-phenyl)-4-(4-trifluoromethoxy-phenylamino)-benzamide

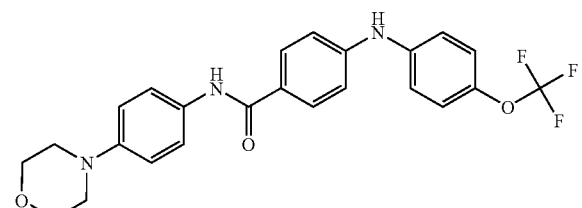

Step 1: Methylene chloride (20 mL) is added to the 4-Morpholinoaniline resin (4.40 g, 3.52 mmol) and the solution is allowed to stand at room temperature for one hour. Triethyl amine (4.9 mL, 35 mmol) is added, followed by 4-chlorobenzoyl chloride (2.24 mL, 17 mmol). The reaction is placed on a shaker and shaken overnight at room temperature. The resin is then filtered and washed consecutively with methanol, N,N-dimethylformamide, and methylene chloride (4×20 mL each). The product is dried under vacuum. A small portion (0.1 g) is cleaved (50% trifluoroacetic acid, 45% methylene chloride, 5% water) for LCMS analysis; MS (ES$^+$) m/e 317.2 (M+H$^+$).

Step 2: The product of step 1 (1.0 g, ~0.8 mmol), 4-(triflouromethoxy)-aniline (0.55 mL, 4.0 mmol), Pd$_2$(dba)$_3$ (0.091 g, 0.10 mmol), and IPrHCl ligand (0.085 g, 0.20 mmol) are placed in a glass vial. Dry dioxane (15 mL) is then added and the vial is filled with nitrogen and sealed. The mixture is shaken overnight at 90° C. After cooling to room temperature, the resin is filtered and washed consecutively with methanol, N,N-dimethylformamide, and methylene chloride (4×10 mL each). The compound is cleaved from the resin (50% trifluoroacetic acid, 45% methylene chloride, 5% water), concentrated and purified by HPLC. The solvent is evaporated, then the fractions are rinsed with toluene (3×20 mL) and concentrated to provide N-(4-Morpholin-4-yl-phenyl)-4-(4-trifluoromethoxy-phenylamino)-benzamide (0.110 g, 30% yield from 4-morpholinoaniline); $^1$H NMR (400 MHz, CDCl$_3$) δ3.36 (m, br, 4H), 4.01 (m, br, 6H), 7.04 (d, J=8.4 Hz, 2H), 7.19 (m, 4H), 7.27 (m, 3H), 7.68 (d, J=8.7 Hz, 2H), 7.79 (d, J=8.5 Hz, 2H), 7.97 (s, 1H); MS (ES$^+$) m/e 458 (M+H$^+$).

By repeating the procedure described in Example 1, using appropriate starting materials, the following compounds of Formula I (examples 2 and 3) are obtained:

EXAMPLE 2

N-(4-Morpholin-4-yl-phenyl)-4-(4-phenoxy-phenylamino)-benzamide

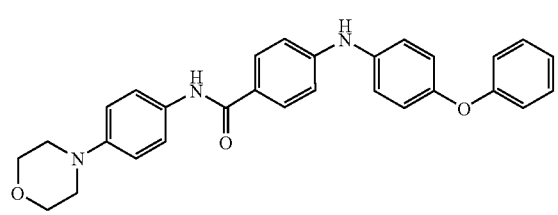

$^1$H NMR (400 MHz, CDCl$_3$) δ3.30 (t, J=4.6 Hz, 4H), 3.97 (t, J=4.6 Hz, 4H), 6.90 (d, J=8.7 Hz, 2H), 6.95 (m, 4H), 7.08 (m, 1H), 7.19 (m, 2H), 7.27 (m, 4H), 7.62 (d, J=8.9 Hz, 2H), 7.70 (d, J=8.7 Hz, 2H), 7.86 (s, 1H); MS (ES$^+$) m/e 466 (M+H$^+$).

EXAMPLE 3

N-[2-(4-Methoxy-phenyl)-ethyl]-4-[4-(3-trifluoromethyl-phenyl)-piperazin-1-yl]-benzamide

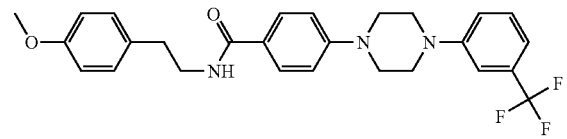

$^1$H NMR (400 MHz, CDCl$_3$) δ2.89 (dd, J=6.7, 6.8 Hz, 2H), 3.49 (m, 8H), 3.70 (m, 2H), 3.83 (s, 3H), 6.08 (m, 1H), 6.89 (m, 2H), 7.03 (m, 2H), 7.20 (m 7.43 (m, 1H), 7.68 (d, J=8.8 Hz, 2H); MS (ES$^+$) m/e 484 (M+H$^+$).

EXAMPLE 4

1-(4-Morpholin-4-yl-phenyl)-3-(4-trifluoromethoxy-phenyl)-urea

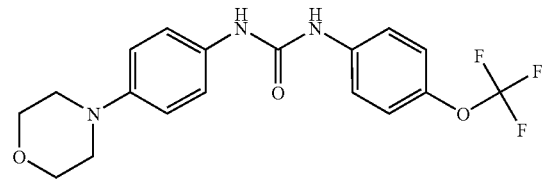

To a solution of 4-morpholinoaniline (270 mg, 1.5 mmol) in dry methylene chloride is added 4-trifluoromethoxy-phenyl isocyanate (229 µl, 1.5 mmol) at room temperature. After stirring at room temperature for 2 hours, the solvent is removed by rotary evaporator. The crude product, 1-(4-Morpholin-4-yl-phenyl)-3-(4-trifluoromethoxy-phenyl)-urea, is recrystallized in methanol to give a white solid (424 mg, 74% yield); $^1$H NMR (400 MHz, d-DMSO) δ3.00 (dd, J=4.7, 4.8 Hz, 4H), 3.71 (dd, J=4.5, 4.9 Hz, 4H), 6.87 (d, J=9.0 Hz, 2H), 7.24 (d, 2H), 7.29 (d, 2H), 7.5 (m, 2H), 8.44 (s, 1H), 8.75 (s, 1H); MS (ES$^+$) m/e 382.1 (M+H$^+$).

EXAMPLE 5

1-(4-Chloro-3-trifluoromethyl-phenyl)-3-(4-morpholin-4-yl-phenyl)-urea

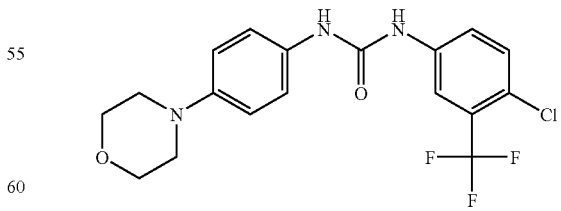

This compound is prepared following the same procedure as Example 4 where 4-chloro-3-(trifluoromethyl)phenyl isocyanate is used instead of 4-trifluoromethoxy-phenyl isocyanate. The final product, 1-(4-Chloro-3-trifluoromethyl-phenyl)-3-(4-morpholin-4-yl-phenyl)-urea, is a dark green solid after recrystallization; $^1$H NMR (400 MHz, d-DMSO) δ3.01 (t, J=4.7 Hz, 4H), 3.71 (dd, J=4.5, 4.9 Hz, 4H), 6.87 (d, J=9.0 Hz, 2H), 7.29 (d, J=9.0 Hz, 2H), 7.58 (m, 2H 8.07 (d, J=2.1 Hz, 1H), 8.56 (s, 1H), 9.04 (s, 1H); MS (ES$^+$) m/e 400.1 (M+H

EXAMPLE 6

3-[6-(4-Trifluoromethoxy-phenylamino)-pyrimidin-4-yl]-N-(2-trifluoromethyl-benzyl)-benzamide

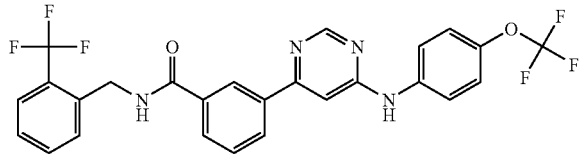

Step A: 4-Chloro-pyrimidin-6-yl-(4-trifluoromethoxy-phenyl)-amine 4,6-Dichloropyrimidine (1.0 g, 6.7 mmol) and p-trifluromethoxy aniline (1.2 g, 6.7 mmol) are dissolved in ethanol (15 mL). DIPEA (1.75 mL, 10 mmol) is then added and the mixture is stirred under reflux condition for 2 hours. After the mixture is cooled down to room temperature, the solvent is evaporated and silica gel column chromatography (at a ratio of ethyl acetate to hexanes of 3:7) gives 4-chloro-pyrimidin-6-yl)-(4-trifluoromethoxy-phenyl)-amine (1.94 g, quantitative).

Step B: 3-[6-(4-Trifluoromethoxy-phenylamino)-pyrimidin-4-yl]-benzoic acid

A mixture of product from Step A (200 mg, 0.69 mmol), 3-carbophenylboronic acid (115 mg, 0.69 mmol), palladium (0) tetrakis triphenylphosphine (40 mg, 0.034 mmol) and sodium carbonate (292 mg, 2.76 mmol) in acetonitrile/water (1:1, 10 mL) is stirred at 90° C. under argon for eight hours. The mixture is cooled to room temperature and solids are filtered off. The remaining liquid is acidified to pH<5 with 6N HCl. Pale white solid forms and is collected by filtration. The solid is washed with water (2×5 mL) and 3-[6-(4-trifluoromethoxy-phenylamino)-pyrimidin-4-yl]-benzoic acid (220 mg, 85% yield) is obtained after drying.

Step C: 3-[6-(4-Trifluoromethoxy-phenylamino)-pyrimidin-4-yl]-N-(2-trifluoromethyl-benzyl)-benzamide A mixture of 3-[6-(4-trifluoromethoxy-phenylamino)-pyrimidin-4-yl]-benzoic acid (100 mg, 0.27 mmol), 2-trifluoromethylbenzyl amine (71 mg, 0.40 mmol), HATU (112 mg, 0.30 mmol) and DIPEA (232 µL, 1.33 mmol) in DMF (4 mL) is stirred at room temperature for eight hours. The solvent is then removed and silica gel chromatography (methanol/dichloromethane, 5/95) affords the title compound, 3-[6-(4-Trifluoromethoxy-phenylamino)-pyrimidin-4-yl]-N-(2-trifluoromethyl-benzyl)-benzamide (134 mg, 95% yield); $^1$H NMR (400 MHz, d-DMSO) δ4.71 (d, J=5.1 Hz, 2H), 7.36 (m, 3H), 7.49 (m, 1H), 7.56 (d, J=7.5 Hz, 1H), 7.67 (m, 2H), 7.75 (d, J=7.9 Hz, 2H), 7.85 (d, J=9.1 Hz, 2H), 8.08 (d, J=7.8 Hz, 1H), 8.23 (d, J=7.7 Hz, 1H), 8.61 (s, 1H), 8.78 (s, 1H), 9.31 (dd, J=5.8, 6.0 Hz, 1H), 9.96 (s, 1H); MS (ES$^+$) m/e 533.1(M+H$^+$).

EXAMPLE 7

4-Methoxy-N-{3-[6-(4-trifluoromethoxy-phenylamino)-pyrimidin-4-yl]-phenyl}-benzenesulfonamide

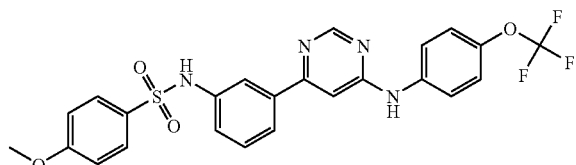

Example 7 is prepared in a similar fashion as example 6; $^1$H NMR (400 MHz, d-DMSO) δ3.78 (s, 3H), 7.06 (m, 2H), 7.22 (m, 1H), 7.24 (m, 1H), 7.40 (m, 3H), 7.66 (m, 1H), 7.72 (m, 2H), 7.85 (m, 3H), 8.75 (s, 1H), 10.06 (m, 1H), 10.42 (s, 1H); MS (ES$^+$) m/e 517.1 (M+H$^+$).

By repeating the procedure described in the above examples, using appropriate starting materials, the following compounds of the invention are obtained:

N-[2-(4-hydroxy-phenyl)-ethyl]-4-[4-(3-trifluoromethyl-phenyl)-piperazin-1-yl]-benzamide;
1-(2,6-dimethoxy-pyridin-3-yl)-3-(4-trifluoromethoxy-phenyl)-urea;
5-(3-amino-phenylcarbamoyl)-2-(3-fluoro-benzoylamino)-4-methyl-thiophene-3-carboxylic acid methyl ester;
furan-2-carboxylic acid [6-(4-tert-butyl-phenoxy)-pyridin-3-yl]-amide;
1-{4-[2-(3-chloro-phenylamino)-pyrimidin-4-yl]-pyridin-2-yl}-1-(3-ureido-propyl)-urea;
2,2-dimethyl-propionic acid 4-[3-(3,4-dimethyl-phenyl)-isoxazol-5-yl]-2H-114-thiazol-2-ylmethyl ester; and
2,2-dimethyl-propionic acid 4-[3-(3,4-dimethyl-phenyl)-isoxazol-5-yl]-thiazol-2-ylmethyl ester.

EXAMPLE 8

The compounds of the invention in free form or in pharmaceutically acceptable salt form, exhibit valuable pharmacological properties, e.g. for tumor or inflammation treatment. The efficacy against tumor cells may be demonstrated in the following way:

Stock solutions of the test compounds (1 mM) are prepared in 100% DMSO and stored at −20° C. Human SW620 colon tumor cells are cultivated using 10% FCS/DMEM (Invitrogen) medium. The cells are plated into 384 well plates at a density of 8000 cells per well in a volume of 50 µL. The cells are placed in a 37° C. incubator and allowed to adhere overnight. Test compounds are added to the cells in a volume of 500 nL (final DMSO concentration in assay is 1%). Serial dilutions of the test compound are added (the top concentration of compound is 10 micromolar (final assay concentration) followed by 11 two fold dilutions. The cells are incubated for a further two days. A solution (50 µL) comprised of 20% alamarBlue™ (Biosource International, Inc.) and 80% assay medium is added to each well and the plates are incubated at 37° C. for a further 4 hours. The plates are read by fluorescence (530 nm excitation, 580 nm emission) on an Acquest reader (LJL Biosystems). The IC50 is defined as the concentration of a test compound at the end of the incubation period, which leads to 50% of cell viability per well compared with the control (concentration at semi-maximum inhibition of cell growth).

Tests on other tumor cell lines are also carried out in a comparable manner: SW480, SW620 and DLD1 (colon tumor cell lines); T3M4, panc-1 (pancreatic tumor cell lines); and A2058 (malignant melanoma cell lines). All results are compared to an identical assay using IOSE-80 cells, which is a preparation of normal human ovarian epithelial cells.

Compounds of the invention were tested according to the above assays for cytotoxicity to one or more cancer cell lines and were observed to exhibit selective cytotoxicity to cancer cell lines but not non-transformed cell lines. For example, N-(4-morpholin-4-yl-phenyl)-4-(4-trifluoromethoxy-phenylamino)-benzamide (example 1) has an $IC_{50}$ of 26 nM in the above assay with the SW620 cell line. Compounds of formula I thus preferably show an $IC_{50}$ in the range of $1\times10^{-10}$ to $1\times10^{-5}$ M, preferably less than 1 µM to one or more tumor cell lines.

Adenosine kinase activity is measured as described by Yamada et al. (Yamada, Y., Goto, H., Ogasawara, N. (1988) Biochim. Biophys. Acta 660, 36–43) and MIF activity is measured as described by Dios, A., et al. (J. Med. Chem. 2002, 45, 2410–2416.

What is claimed is:

1. A compound selected from: N-(4-Morpholin-4-yl-phenyl)-4-(4-trifluoromethoxy-phenylamino)-benzamide; N-(4-Morpholin-4-yl-phenyl)-4-(4-phenoxy-phenylamino)-benzamide; N-[2-(4-Methoxy-phenyl)-ethyl]-4-[4-(3-trifluoromethyl-phenyl)-piperazin-1-yl]-benzamide; 3-[6-(4-Trifluoromethoxy-phenylamino)-pyrimidin-4-yl]-N-(2-trifluoromethyl-benzyl)-benzamide; and N-[2-(4-hydroxy-phenyl)-ethyl]-4-[4-(3-trifluoromethyl-phenyl)-piperazin-1-yl]-benzamide.

* * * * *